United States Patent [19]

Wehinger et al.

[11] Patent Number: 4,568,681
[45] Date of Patent: Feb. 4, 1986

[54] ANTIHYPERTENSIVE TETRAHYDROPYRIDINE 3,5 DICARBOXYLIC ACID ESTERS

[75] Inventors: Egbert Wehinger; Stanislav Kazda; Andreas Knorr, all of Wuppertal, Fed. Rep. of Germany

[73] Assignee: Bayer Aktiengesellschaft, Leverkusen, Fed. Rep. of Germany

[21] Appl. No.: 538,683

[22] Filed: Oct. 3, 1983

[30] Foreign Application Priority Data

Oct. 23, 1982 [DE] Fed. Rep. of Germany ....... 3239273

[51] Int. Cl.[4] .................. C07D 211/78; C07D 401/12; C07D 405/02; A61K 31/455
[52] U.S. Cl. ................................... 514/332; 514/333; 514/338; 514/356; 546/256; 546/263; 546/270; 546/321
[58] Field of Search ............... 546/321, 257, 283, 275, 546/284, 278, 273, 279, 270, 280, 271, 281, 167, 144, 139, 256, 263; 424/266, 251, 250, 258; 544/238, 284, 333, 353, 405; 514/332, 333, 338, 356

[56] References Cited

PUBLICATIONS

Chatterjea, J. N., "1,3-Dimethyl-2-Azafluorenore Meyer's Pyridine Synthesis", Chemical Abstracts 47:9972.

Bossert, F. et al., "4-Aryldihydropyridines", Angew. Chem. Int. Ed. Engl. 20, pp. 762–769 (1981).

Schramm, M. et al., "Novel Dihydropyridines with Positive Inotropic Action Through Activation of Ca$^{2+}$ Channels", Nature, vol. 303, (Jun. 9, 1983), pp. 535–537.

Primary Examiner—Henry R. Jiles
Assistant Examiner—Dale A. Bjorkman
Attorney, Agent, or Firm—Sprung Horn Kramer & Woods

[57] ABSTRACT

1,2,3,4-Tetrahydropyridines of the formula

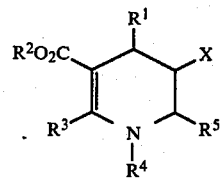

in which
$R^1$ is optionally substituted aryl or heterocyclic,
$R^2$ is an organic radical,
X is a nitrile or ester,
$R^3$ and $R^5$ are identical or different and each represent hydrogen, a straight-chain or branched or salts thereof with physiologically tolerated acids are antihypertensives.

9 Claims, No Drawings

ANTIHYPERTENSIVE TETRAHYDROPYRIDINE 3,5 DICARBOXYLIC ACID ESTERS

The present invention relates to new tetrahydropyridines, to a process for their preparation and to their use in medicaments, especially in agents affecting the circulation.

The new 1,2,3,4-tetrahydropyridines are characterized by the general formula(I)

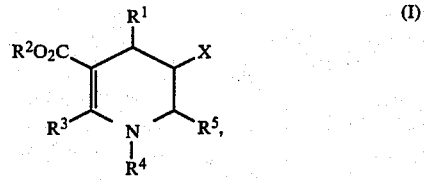

in which $R^1$ represents aryl or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, the aryl radical optionally containing 1 to 2 identical or different substituents from the group comprising phenyl, alkyl, alkoxy, alkylene, dioxyalkylene, halogen, trifluoromethyl, polyfluoroalkoxy or cyano;

$R^2$ represents a straight-chain, branched or cyclic, saturated or unsaturated hydrogen radical, which is optionally interrupted by an oxygen or sulphur atom in the chain and/or which is optionally substituted by halogen, cyano, hydroxyl, pyridyl, phenyl-, phenoxy- or phenylthio, it being possible for the phenyl groups in turn to be substituted by halogen, cyano, dialkylamino, alkoxy, alkyl, trifluoromethyl or polyfluoroalkoxy, or by an amino group which is substituted by two identical or different substituents from the group comprising alkyl, aryl or aralkyl, $R^3$ and $R^5$ are identical or different and each represent hydrogen, a straight-chain or branched alkyl radical, an aryl radical or an aralkyl radical, $R^4$ represents hydrogen, a straight-chain or branched alkyl radical, which is optionally interrupted by an oxygen atom, an aryl radical or an aralkyl radical and X denoted either the nitrile group or the radical —$CO_2R^6$, wherein $R^6$ corresponds to the definition of $R^2$ and can be both identical to $R^2$ and different from $R^2$, and their salts with appropriate physiologically tolerated acids.

Furthermore, it has been found that the compounds of the formula (I) according to the invention are obtained when dihydropyridine compounds of the formula (II)

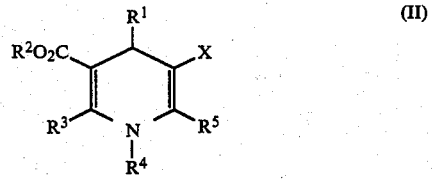

in which $R^1$, $R^2$, $R^3$, $R^4$, $R^5$ and X have the abovementioned meaning, are electrically reduced at a cathode in the presence of a suitable electrolyte system.

In the case where $R^4$ in formula (I) denotes hydrogen, it is also possible to use, as the starting material for the electrochemical reduction, the pyridine derivatives of the formula (III),

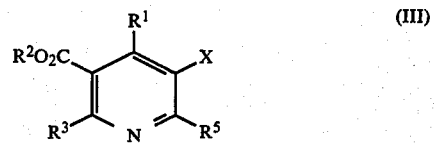

in which the substituents $R^1$, $R^2$, $R^3$, $R^5$ and X have the abovementioned meaning.

The 1,2,3,4-tetrahydropyridine derivatives according to the invention have valuable pharmacological properties. Because of their effect on the circulation, they can be used as antihypertensive agents, as peripheral and cerebral vasodilators and as coronary therapeutic agents and thus are to be regarded as an enrichment of pharmacy.

Depending on the nature of the starting materials used, the preparation of the compounds according to the invention can be represented by the following reaction schemes in which dimethyl 2,6-dimethyl-4-phenyl-1,2,3,4-tetrahydropyridine-3,5-dicarboxylate may be chosen as an example:

(A)

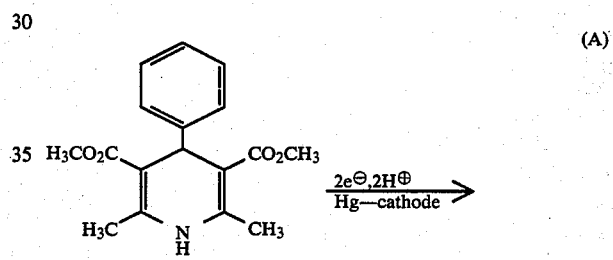

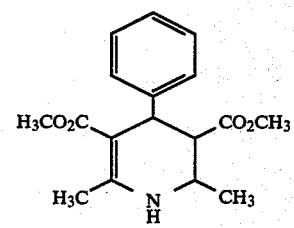

(B)

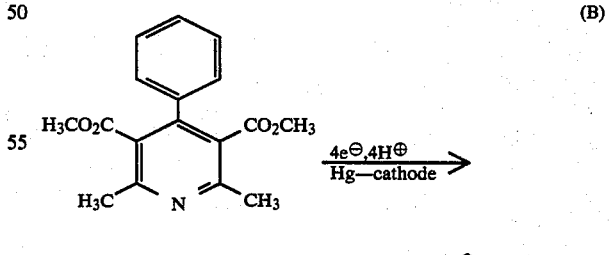

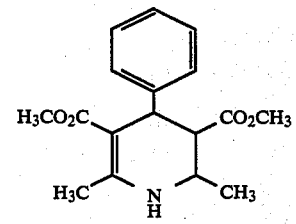

According to process A, a 1,4-dihydropyridine derivative of the general formula (II)

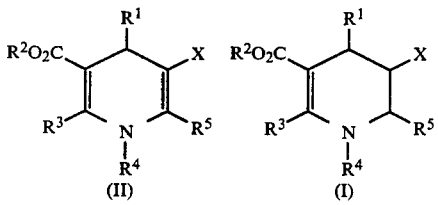

is converted on a mercury cathode in a suitable electrolyte system into a 1,2,3,4-tetrahydropyridine derivative of the formula (I) according to the invention.

In the formulae (I) and (II), $R^1$ preferably represents phenyl, naphthyl or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, it being possible for each of the carbocycles mentioned to be substituted by 1 or 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, tri- tetra- and pentamethylene, dioxamethylene, halogen, trifluoromethyl, trifluoromethoxy, difluoromethoxy, tetrafluoroethoxy or cyano, $R^2$ preferably represents a straight-chain, branched or cyclic, saturated or unsaturated hydrocarbon radical having up to 20 carbon atoms, which is optionally interrupted by one oxygen or sulphur atom in the chain and/or which is optionally substituted by halogen, in particular by fluorine or chlorine, cyano, hydroxyl, α-, β- or γ-pyridyl, phenyl, phenoxy or phenylthio, it being possible for the phenyl groups to be substituted by halogen, in particular fluorine or chlorine, by cyano, dialkylamino having 1 to 4 carbon atoms in each alkyl radical, alkoxy having 1 to 4 carbon atoms, alkyl having 1 to 4 carbon atoms, trifluoromethyl or trifluoromethoxy, or by an amino group which in turn is substituted by two identical or different substituents from the group comprising alkyl having 1 to 4 carbon atoms, phenyl or benzyl, $R^3$ and $R^5$, which are identical or different, each preferably represent hydrogen, a straight-chain or branched alkyl radical having up to 4 carbon atoms, a phenyl radical or a benzyl radical, $R^4$ preferably represents hydrogen, a straight-chain or branched alkyl radical having up to 4 carbon atoms which is optionally interrupted by an oxygen atom, a phenyl radical or a benzyl radical and X preferably represents the nitrile group or the radical $-CO_2R^6$, $R^2$ and $R^6$ being identical or different and corresponding to one another in their range of definition.

Compounds of the general formula (I) are of particular interest in which $R^1$ represents phenyl or pyridyl, the phenyl ring optionally being substituted by one or two identical or different substituents from the group comprising fluorine, chlorine, cyano, trifluoromethyl, trifluoromethoxy, alkyl having 1 to 4 C atoms, alkoxy having 1 to 2 C atoms, tetramethylene or phenyl, $R^2$ represents a straight-chain or branched cyclic alkyl or alkenyl radical having up to 12 carbon atoms which is optionally interrupted by an oxygen atom in the chain and/or which is optionally substituted by fluorine, chlorine, cyano, hydroxyl, phenyl, phenoxy or an amino group which in turn is substituted by two identical or different substituents from the group comprising alkyl having 1 to 4 C atoms or benzyl, $R^3$ and $R^5$ are idential or different and each represent alkyl having 1 to 2 C atoms, $R^4$ represents hydrogen, alkyl having 1 to 4 C atoms or benzyl and X represents the nitrile group or represents the radical $-CO_2R^6$, $R^6$ having the meaning of $R^2$ and being identical to or different from $R^2$.

The derivatives of the general formulae (II) and (III) used as starting materials are known from the literature or can be prepared by methods known from the literature (compare, for example, U. Eisner and J. Kuthan, Chem. Rev. 72, 1 (1972); E. Wehinger, F. Bossert, G. Franckowiak and H. Meyer, German Offenlegungsschrift (German Published Specification) No. 2,658,804, publication date: 6.7.1978).

The following may be mentioned as examples:
diethyl 1,4-dihydro-2,6-dimethyl-4-(3-chlorophenyl)-pyridine-3,5-dicarboxylate,
di-(n)-butyl 1,4-dihydro-2,6-dimethyl-4-(2-chlorophenyl)-pyridine-3,5-dicarboxylate,
dihexyl 1,4-dihydro-2,6-dimethyl-4-(2-chlorophenyl)-pyridine-3,5-dicarboxylate,
didecyl 1,4-dihydro-2,6-dimethyl-4-(2-chlorophenyl)-pyridine-3,5-dicarboxylate,
diisopropyl 1,4-dihydro-2,6-dimethyl-4-(3-trifluoromethylphenyl)-pyridine-3,5-dicarboxylate,
di-tert.-butyl 1,4-dihydro-2,6-dimethyl-4-(2-methoxyphenyl)-pyridine-3,5-dicarboxylate,
dicyclopentyl 1,4-dihydro-2,6-dimethyl-4-(3-methylphenyl)-pyridine-3,5-dicarboxylate,
diallyl 1,4-dihydro-2,6-dimethyl-4-(3-cyanophenyl)-pyridine-3,5-dicarboxylate,
dimethyl 1,4-dihydro-2,6-dimethyl-4-(3,4-dioxymethylenephenyl)-pyridine-3,5-dicarboxylate,
dibenzyl 1,4-dihydro-2,6-dimethyl-4-(2,3-dichlorophenyl)-pyridine-3,5-dicarboxylate,
bis-(2-methoxyethyl) 1,4-dihydro-2,6-dimethyl-4-(2-trifluoromethoxyphenyl)-pyridine-3,5-dicarboxylate,
bis-(2-phenoxyethyl) 1,4-dihydro-2,6-dimethyl-4-(2-fluorophenyl)-pyridine-3,5-dicarboxylate,
dimethyl 1,4-dihydro-2,6-diethyl-4-(3-fluorophenyl)-pyridene-3,5-dicarboxylate,
bis-(2-phenylthioethyl) 1,4-dihydro-2,6-dimethyl-4-(2,3-dimethylphenyl)-pyridine-3,5-dicarboxylate,
bis-(pyridyl-2-methyl) 1,4-dihydro-2,6-dimethyl-4-(2,3-dichlorophenyl)-pyridine-3,5-dicarboxylate,
bis-(2-dimethylaminoethyl) 1,4-dihydro-2,6-dimethyl-4-(2-methoxyphenyl)-pyridine-3,5-dicarboxylate,
bis-[2-(N-benzyl-N-methylamino)-ethyl] 1,4-dihydro-2,6-dimethyl-4-(2-chlorophenyl)-pyridine-3,5-dicarboxylate,
dimethyl 1,4-dihydro-2,6-dipropyl-4-(2-cyclophenyl)-pyridine-3,5-dicarboxylate,
isopropyl 3-cyano-1,4-dihydro-2,6-dimethyl-4-(3,4-dimethoxyphenyl)-pyridine-5-carboxylate,
cyclopentyl 3-cyano-1,4-dihydro-2,6-dimethyl-4-(2-fluoro-3-chlorophenyl)-pyridine-5-carboxylate,
2-phenoxyethyl 3-cyano-1,4-dihydro-2,6-dimethyl-4-(2,3-tetramethylenephenyl)-pyridine-5-carboxylate,
2-dimethylaminoethyl 3-cyano-1,4-dihydro-2,6-dimethyl-4-(2-fluorophenyl)-pyridine-5-carboxylate and 2-(N-benzyl-N-methylamino)-ethyl 3-cyano-1,4-dihydro-2,6-dimethyl-4-(2,3-dihlorophenyl)-pyridine-5-carboxylate.

In order to carry out the process according to the invention, a divided electrolysis cell having a conventional cathode, in particular having a pool of mercury as the cathode, and a conventional anode, in particular a sheet of platinum or graphite as the anode, is preferably used (compare, for example, N. L. Weinberg, Technique of Electroorganic Synthesis, Part I, John Wiley & Sons, (1974)).

Protic solvents, such as water, methanol, ethanol or mixtures of these, are primarily suitable as the reaction medium. In addition, aprotic solvents, such as acetonitrile or dimethylformamide, can also be employed with advantage when they are diluted with water or another proton donor.

Alkali metal or tetralkylammonium salts have been found particularly suitable as conducting salts, lithium tetrafluoroborate, tetraethylammonium tetrafluoroborate or tetrabutylammonium chloride being mentioned as preferred examples.

The reaction is preferably carried out under an atmosphere of inert gas, such as, for example, nitrogen or a noble gas.

The reaction temperature can be varied widely, but the range of 0°–50° C., in particular 10° to 30° C., has proved to be particularly advantageous.

The reaction can be carried out both galvanostatically and potentiostatically. In the potentiostatic embodiment, depending on the substrate, electrolysis is carried on at a cathode potential of about −1.8 to −2.5 V (measured against saturated calomel electrode) until the current approaches zero or until the required amount of charge (2 faraday per mol of 1,4-dihydropyridine of the formula (II)) has flowed through the circuit. The catholyte is then evaporated in vacuo, the conducting salt is removed by the conventional methods of work-up and the substance according to the invention is purified.

When $R^4$ in the formula (I) denotes hydrogen, it is also possible to use, in process variant B, the pyridine derivatives of the general formula (III), in which the substituents $R^1$, $R^2$, $R^3$, $R^5$ and X have the abovementioned meaning, as the substrate of the electrochemical reduction.

Process variant B is carried out entirely in analogy to process variant A with the oily difference that, according to its nature, 4 faraday-equivalents are necessary per mol of pyridine derivative.

Every modification of this process, especially changes in the electrolyte system in respect of nature, quantitative composition of the components and pH, can be used in the same manner for the preparation of the compounds according to the invention.

Depending on the nature of the radicals $R^1$ to $R^5$ and X, the compounds according to the invention contain at least 3 centers of asymmetry and can thus occur in several stereoisomeric forms. The present invention relates to both the antipodes and racemic forms as well as to the mixtures of diastereiomers. The racemic forms can be separated, as can be diasteriomers, into the homogeneous stereoisomeric constituents in a known manner (compare, for example, E. L. Eliel, Stereochemistry of Carbon Compounds, McGraw Hill, (1962)).

Apart from the preparation examples listed below, the following active compounds according to the invention may be mentioned:

diethyl 2,6-dimethyl-4-(2-trifluoromethylphenyl)-1,2,3,4-tetrahydropyridine-3,5-dicarboxylate, dibutyl 2,6-dimethyl-4-(2-trifluoromethylphenyl)-1,2,3,4-tetrahydropyridine-3,5-dicarboxylate, didecyl 2,6-dimethyl-4-(2-trifluoromethylphenyl)-1,2,3,4-tetrahydropyridine-3,5-dicarboxylate, diisopropyl 2,6-dimethyl-4-(2-chlorophenyl)-1,2,3,4-tetrahydropyridine-3,5-dicarboxylate, dicyclopentyl 2,6-dimethyl-4-(2,3-dichlorophenyl)-1,2,3,4-tetrahydropyridine-3,5-dicarboxylate, diallyl 2,6-dimethyl-4-(2-methoxyphenyl)-1,2,3,4-tetrahydropyridine-3,5-dicarboxylate, dibenzyl 2,6-dimethyl-4-(3-methylphenyl)-1,2,3,4-tetrahydropyridine-3,5-dicarboxylate, bis-(2-methoxyethyl) 2,6-dimethyl-4-(2-trifluoromethoxyphenyl)-1,2,3,4-tetrahydropyridine-3,5-dicarboxylate, bis-(2-phenoxyethyl) 2,6-dimethyl-4-(2-fluoro-3-chlorophenyl)-1,2,3,4-tetrahydropyridine-3,5-dicarboxylate, dimethyl 2,6-diethyl-4-(3-chlorophenyl)-1,2,3,4-tetrahydropyridine-3,5-dicarboxylate, diethyl 2,6-diethyl-4-(2-chlorophenyl)-1,2,3,4-tetrahydropyridine-3,5-dicarboxylate, 5-ethyl 3-methyl 2,6-dimethyl-4-(2,3-dichlorophenyl)-1,2,3,4-tetrahydropyridine-3,5-dicarboxylate, 3-ethyl 5-methyl 2,6-dimethyl-4-(2,3-dichlorophenyl)-1,2,3,4-tetrahydropyridine-3,5-dicarboxylate, 5-isopropyl 3-methyl 2,6-dimethyl-4-(2,3-dichlorophenyl)-1,2,3,4-tetrahydropyridine-3,5-dicarboxylate, 5-(2-(N-benzyl-N-methylamino)-ethyl) 3-methyl 2,6-dimethyl-4-(2-chlorophenyl)-1,2,3,4-tetrahydropyridine-3,5-dicarboxylate and 5-isopropyl 3-(2-methoxyethyl) 2,6-dimethyl-4-(2-chloro-3-methoxyphenyl)-1,2,3,4-tetrahydropyridine-3,5-dicarboxylate.

The new compounds have a broad and versatile spectrum of pharmacological activity.

In detail, the following main effects have been demonstrated in animal experiments:

1. On parenteral, oral and perlingual administration, the compounds bring about a marked and long-lasting dilation of the coronary vessels. This effect on the coronary vessels is potentiated by a simultaneous cardiac-relieving effect resembling nitries.

They affect or change the cardiac metabolism in the sense of saving energy.

2. The excitability of the impulse-forming and conduction systems within the heart is decreased so that a detectable antifibrillatory activity results at therapeutic doses.

3. The tone of the smooth muscle of the vessels is greatly decreased under the action of the compounds. This vasospasmolytic effect can take place in the entire vascular system or can manifest itself in a manner more or less isolated in restricted vascular regions (such as, for example, the central nervous system). Thus the compounds are particularly suitable as cerebral therapeutic agents.

4. Compounds lower the blood pressure of normotensive and hypertensive animals and can thus be used as antihypertensive agents.

5. Compounds have strong myospasmolytic effects which are marked on the smooth muscle of the stomach, intestinal tract, urogenital tract and respiratory tract.

Due to these properties, the compounds according to the invention are particularly suitable for the prophylaxis and therapy of acute and chronic ischaemic heart disease in its widest meaning, for the therapy of hypertension and for the treatment of disturbances of cerebral and peripheral blood flow.

The new active compounds can be converted in a known manner into the conventional formulations, such as tablets, capsules, coated tablets, pills, granules, aerosols, syrups, emulsions, suspensions and solutions, using inert, non-toxic, pharmaceutically suitable vehicles or salts. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents and, for example, when using water as a diluent, organic solvents can optionally be used as auxiliary solvents.

Examples of auxiliaries which may be mentioned are:

Water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid vehicles, such as, for example, natural rock powders (for example kaolins, aluminas, talc and chalk), synthetic rock powders (for example highly disperse silica and silicates), sugars (for example crude sugar, lactose and glucose), emulsifiers (for example polyoxyethylene-fatty acid esters, polyoxyethylene-fatty alcohol ethers, alkyl sulphonates and aryl sulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can be co-used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 10 mg/kg, preferably 0.05 to 5 mg/kg, of body weight daily to achieve effective results and, in the case of oral administration, the dosage is about 0.05 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the abovementioned minimum amount, while in other cases the upper limit mentioned must be exceeded.

Where relatively large amounts are administered, it can be advisable to divide these into several individual administration over the course of the day. The same dosage range is envisaged for administration in human medicine. In this connection, the above statements similarly apply.

PREPARATION EXAMPLES

Example 1

Dimethyl 2,6-dimethyl-4-phenyl-1,2,3,4-tetrahydropyridine-3,5-dicarboxylate

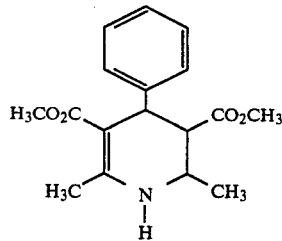

5 g (17 mmols) of dimethyl 1,4-dihydro-2,6-dimethyl-4-phenylpyridine-3,5-dicarboxylate in 170 ml of a 0.1 molar solution of tetraethylammonium tetrafluoroborate in methanol were electrolyzed in a divided electrolysis cell (see N. L. Weinberg, Technique of Electroorganic Synthesis, Part I, John Wiley & Sons, (1974)) having a mercury cathode and a platinum sheet anode at a cathode potential of $-2.0$ V (against a saturated calomel electrode (SCE)), at 25° C. and under a nitrogen atmosphere. The same supporting electrolyte was used for the cathode and anode chambers.

After an amount of charge of 3,300 coulomb (34 mmol $e° \hat{=} 2$ faraday equivalents) had flowed through, the current approached zero. The anolyte was discarded and the catholyte was evaporated in vacuo after separating off the mercury. The residue was taken up in dichloromethane, the organic phase was washed several times with water and, after drying over anhydrous sodium sulphate, was distilled under reduced pressure. The remaining oil solidified on trituration with ether, it was filtered off with suction and recrystallized from methanol.

Melting point: 165°–167° C., yield: 2 g (39%).

Example 2

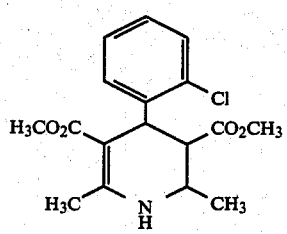

In analogy to Example 1, dimethyl 2,6-dimethyl-4-(2-chlorophenyl)-1,2,3,4-tetrahydropyridine-3,5-dicarboxylate was obtained by cathodic reduction of dimethyl 1,4-dihydro-2,6-dimethyl-4-(2-chlorophenyl)-pyridine-3,5-dicarboxylate in methanol/tetraethylammonium tetrafluoroborate, melting point: 128°–130° C., yield: 54%.

Example 3

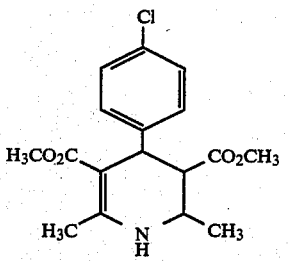

In analogy to Example 1, dimethyl 2,6-dimethyl-4-(4-chlorophenyl)-1,2,3,4-tetrahydropyridine-3,5-dicarboxylate was obtained by reduction of dimethyl 1,4-dihydro-2,6-dimethyl-4-(4-chlorophenyl)-pyridine-3,5-dicarboxylate at a mercury cathode in methanol/tetraethylammonium tetrafluoroborate, melting point: 186°–188° C., yield: 62%.

Example 4

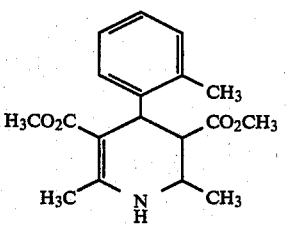

In analogy to Example 1, dimethyl 2,6-dimethyl-4-(2-methylphenyl)-1,2,3,4-tetrahydropyridine-3,5-dicarboxylate was obtained by reduction of dimethyl 1,4-dihydro-2,6-dimethyl-4-(2-methylphenyl)-pyridine-3,5-dicarboxylate at a mercury cathode in methanol/tetraethylammonium tetrafluoroborate, melting point: 125°–127° C., yield: 53%.

Example 5

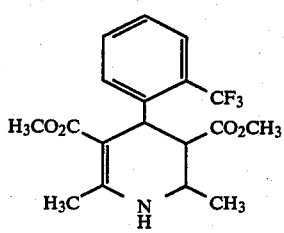

In analogy to Example 1, dimethyl 2,6-dimethyl-4-(2-trifluoromethylphenyl)-1,2,3,4-tetrahydropyridine-3,5-dicarboxylate was obtained by cathodic reduction of dimethyl 1,4-dihydro-2,6-dimethyl-4-(2-trifluoromethylphenyl)-pyridine-3,5-dicarboxylate at a mercury electrode in methanol/tetraethylammonium tetrafluoroborate, melting point 178°–181° C., yield: 62% of theory.

Example 6

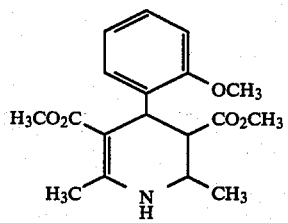

In analogy to Example 1, dimethyl 2,6-dimethyl-4-(2-methoxyphenyl)-1,2,3,4-tetrahydropyridine-3,5-dicarboxylate was obtained by reduction of dimethyl 1,4-dihydro-2,6-dimethyl-4-(2-methoxyphenyl)-pyridine-3,5-dicarboxylate at a mercury cathode in methanol/tetraethylammonium tetrafluoroborate, melting point: 197°–199° C., yield: 67%.

Example 7

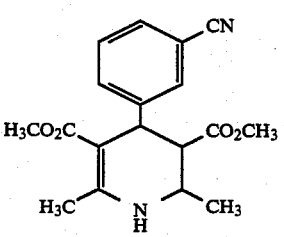

In analogy to Example 1, dimethyl 2,6-dimethyl-4-(3-cyanophenyl)-1,2,3,4-tetrahydropyridine-3,5-dicarboxylate was obtained by reduction of dimethyl 1,4-dihydro-2,6-dimethyl-4-(3-cyanophenyl)-pyridine-3,5-dicarboxylate at a mercury cathode in methanol/tetraethylammonium tetrafluoroborate, melting point 170°–173° C., yield: 35%.

Example 8

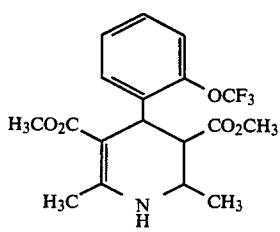

In analogy to Example 1, dimethyl 2,6-dimethyl-4-(2-trifluoromethoxyphenyl)-1,2,3,4-tetrahydropyridine-3,5-dicarboxylate was obtained by reduction of dimethyl 1,4-dihydro-2,6-dimethyl-4-(2-trifluoromethoxyphenyl)-pyridine-3,5-dicarboxylate at a mercury cathode in methanol/tetraethylammonium tetrafluoroborate, melting point: 145° C., yield: 32%.

Example 9

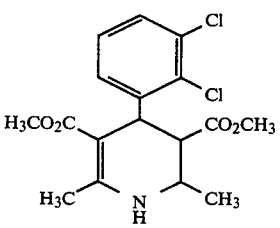

In analogy to Example 1, dimethyl 2,6-dimethyl-4-(2,3-dichlorophenyl)-1,2,3,4-tetrahydropyridine-3,5-dicarboxylate was obtained by reduction of dimethyl 1,4-dihydro-2,6-dimethyl-4-(2,3-dichlorophenyl)-pyridine-3,5-dicarboxylate at a mercury cathode in methanol/tetraethylammonium tetrafluoroborate, melting point: 170°-172° C., yield: 64%.

Example 10

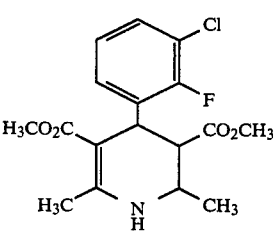

In analogy to Example 1, dimethyl 2,6-dimethyl-4-(2-fluoro-3-chlorophenyl)-1,2,3,4-tetrahydropyridine-3,5-dicarboxylate was obtained by cathodic reduction of dimethyl 1,4-dihydro-2,6-dimethyl-4-(2-fluoro-3-chlorophenyl)-pyridine-3,5-dicarboxylate at a mercury electrode in methanol/tetraethylammonium tetrafluoroborate, melting point: 172°-174° C., yield: 38%.

Example 11

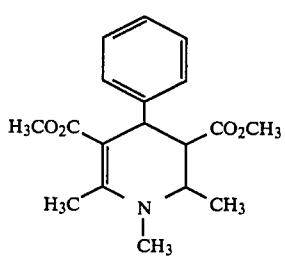

In analogy to Example 1, dimethyl 1,2,6-trimethyl-4-phenyl-1,2,3,4-tetrahydropyridine-3,5-dicarboxylate was obtained by reduction of dimethyl 1,4-dihydro-1,2,6-trimethyl-4-phenylpyridine-3,5-dicarboxylate at a mercury cathode in methanol/tetraethylammonium tetrafluoroborate, melting point: 89°-90° C., yield: 29%.

Example 12

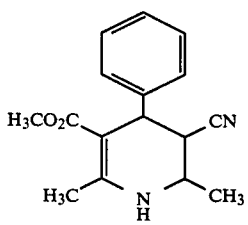

In analogy to Example 1, methyl 3-cyano-2,6-dimethyl-4-phenyl-1,2,3,4-tetrahydropyridine-5-carboxylate was obtained by reduction of methyl 3-cyano-1,4-dihydro-2,6-dimethyl-4-phenylpyridine-5-carboxylate at a mercury cathode in methanol/tetraethylammonium tetrafluoroborate, melting point: 170°-172° C., yield: 45%.

Example 13

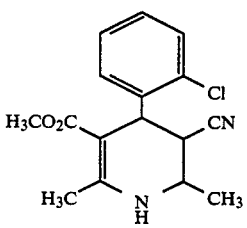

In analogy to Example 1, methyl 3-cyano-2,6-dimethyl-4-(2-chlorophenyl)-1,2,3,4-tetrahydropyridine-5-carboxylate was obtained by reduction of methyl 3-cyano-1,4-dihydro-2,6-dimethyl-4-(2-chlorophenyl)-pyridine-5-carboxylate at a mercury cathode in methanol/tetrabutylammonium tetrafluoroborate, melting point: 168°-170° C., yield: 71%.

Example 14

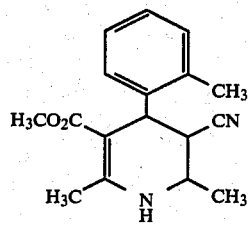

In analogy to Example 1, methyl 3-cyano-2,6-dimethyl-4-(2-methylphenyl)-1,2,3,4-tetrahydropyridine-5-carboxylate was obtained by cathodic reduction of methyl 3-cyano-1,4-dihydro-2,6-dimethyl-4-(2-methylphenyl)-pyridine-5-carboxylate at a mercury electrode in methanol/lithium tetrafluoroborate, melting point: 194°–196° C., yield: 53%.

Example 15

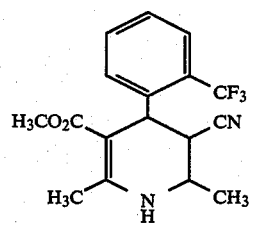

In analogy to Example 1, methyl 3-cyano-2,6-dimethyl-4-(2-trifluoromethylphenyl)-1,2,3,4-tetrahydropyridine-5-carboxylate was obtained by cathodic reduction of methyl 3-cyano-1,4-dihydro-2,6-dimethyl-4-(2-trifluoromethylphenyl)-pyridine-5-carboxylate at a mercury electrode in aqueous methanol/tetraethylammonium tetrafluoroborate, melting point: 202°–204° C., yield: 59%.

Example 16

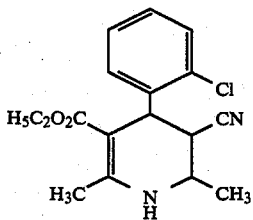

In analogy to Example 1, ethyl 3-cyano-2,6-dimethyl-4-(2-chlorophenyl)-1,2,3,4-tetrahydropyridine-5-carboxylate was obtained by cathodic reduction of ethyl 3-cyano-1,4-dihydro-2,6-dimethyl-4-(2-chlorophenyl)-pyridine-5-carboxylate in ethanol/tetraethylammonium tetrafluoroborate, melting point: 184°–186° C., yield: 60%.

Example 17

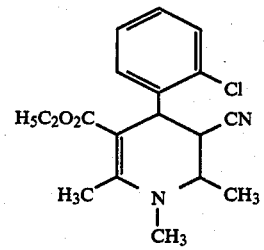

In analogy to Example 1, ethyl 3-cyano-1,2,6-trimethyl-4-(2-chlorophenyl)-1,2,3,4-tetrahydropyridine-5-carboxylate was obtained by cathodic reduction of ethyl 3-cyano-1,4-dihydro-1,2,6-trimethyl-4-(2-chlorophenyl)-pyridine-5-carboxylate at a mercury electrode in methanol/tetraethylammonium tetrafluoroborate, melting point: 147°–148° C., yield: 30%.

Example 18

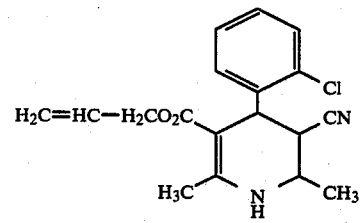

In analogy to Example 1, allyl 3-cyano-2,6-dimethyl-4-(2-chlorophenyl)-1,2,3,4-tetrahydropyridine-5-carboxylate was obtained by reduction of allyl 3-cyano-1,4-dihydro-2,6-dimethyl-4-(2chlorophenyl)-pyridine-5-carboxylate at a mercury electrode in methanol/tetraethylammonium tetrafluoroborate, melting point: 158°–159° C., yield: 35%.

Example 19

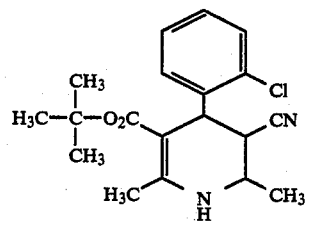

In analogy to Example 1, tert.-butyl 3-cyano-2,6-dimethyl-4-(2-chlorophenyl)-1,2,3,4-tetrahydropyridine-5-carboxylate was obtained by reduction of tert.-butyl 3-cyano-1,4-dihydro-2,6-dimethyl-4-(2-chlorophenyl)-pyridine-5-carboxylate at a mercury cathode in methanol/tetraethylammonium tetrafluoroborate, melting point: 204°–205° C., yield: 32%.

Example 20

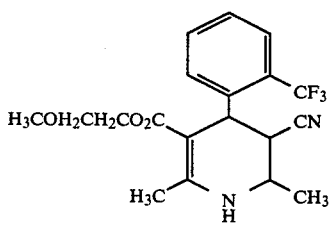

In analogy to Example 1, 2-methoxyethyl 3-cyano-2,6-dimethyl-4-(2-trifluoromethylphenyl)-1,2,3,4-tetrahydropyridine-5-carboxylate was obtained by reduction of 2-methoxyethyl 3-cyano-1,4-dihydro-2,6-dimethyl-4-(2-trifluoromethylphenyl)-pyridine-5-carboxylate at a mercury cathode in a 1:1 mixture of methanol/acetonitrile/tetraethylammonium tetrafluoroborate, melting point: 182°–183° C., yield: 54%.

Example 21

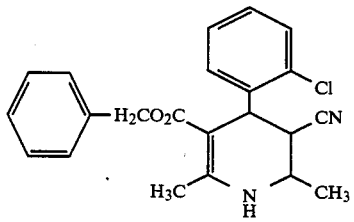

In analogy to Example 1, benzyl 3-cyano-2,6-dimethyl-4-(2-chlorophenyl)-1,2,3,4-tetrahydropyridine-5-carboxylate was obtained by cathodic reduction of benzyl 3-cyano-1,4-dihydro-2,6-dimethyl-4-(2-chlorophenyl)-pyridine-5-carboxylate at a mercury electrode in methanol/tetraethylammonium tetrafluoroborate, melting point: 194°–196° C., yield: 45%.

Example 22

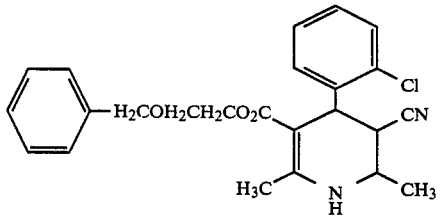

In analogy to Example 1, 2-benzyloxyethyl 3-cyano-2,6-dimethyl-4-(2-chlorophenyl)-1,2,3,4-tetrahydropyridine-5-carboxylate was obtained by cathodic reduction of 2-benzyloxyethyl 3-cyano-1,4-dihydro-2,6-dimethyl-4-(2-chlorophenyl)-pyridine-5-carboxylate at a mercury electrode in methanol/acetonitrile/tetraethylammonium tetrafluoroborate, melting point: 88°–90° C., yield: 25%.

Example 23

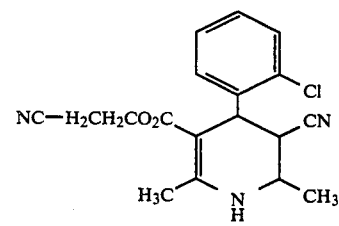

In analogy to Example 1, 2-cyanoethyl 3-cyano-2,6-dimethyl-4-(2-chlorophenyl)-1,2,3,4-tetrahydropyridine-5-carboxylate was obtained by reduction of 2-cyanoethyl 3-cyano-1,4-dihydro-2,6-dimethyl-4-(2-chlorophenyl)-pyridine-5-carboxylate at a mercury cathode in methanol/tetraethylammonium tetrafluoroborate, melting point: 189°–191° C., yield: 25%.

Example 24

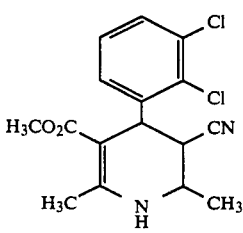

In analogy to Example 1, methyl 3-cyano-2,6-dimethyl-4-(2,3-dichlorophenyl)-1,2,3,4-tetrahydropyridine-5-carboxylate was obtained by reduction of methyl 3-cyano-1,4-dihydro-2,6-dimethyl-4-(2,3-dichlorophenyl)-pyridine-5-carboxylate at a mercury cathode in methanol/tetraethylammonium tetrafluoroborate, melting point: 238°–240° C., yield: 45%.

What is claimed is:
1. A 1,2,3,4-tetrahydropyridine of the formula

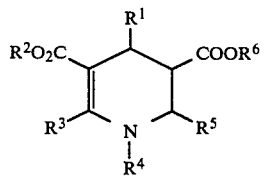

in which $R^1$ represents phenyl or naphthyl optionally substituted by 1 or 2 identical or different substituents from the group consisting of phenyl, straight-chain or branched alkyl having 1 to 8 carbon atoms, cycloalkyl having 3 to 7 carbon atoms, alkoxy having 1 to 4 carbon atoms, tri-tetra-and penta-methylene, dioxamethylene, halogen, trifluoromethyl, trifluoromethoxy, difluoromethoxy, tetrafluoroethoxy or cyano $R^2$ and $R^6$ are identical or are different and represent a straight-chain, branched or cyclic, saturated or unsaturated hydrocarbon radical having up to 20 carbon atoms, which is optionally interrupted by one oxygen or sulphur atom in the chain and/or which is optionally substituted by halogen, cyano, hydroxyl, α-, β- or γ-pyridyl, phenyl, phenoxy or phenylthio, it being possible for the phenyl groups to be substituted by halogen, cyano, dialkylamino having 1 to 4 carbon atoms in each alkyl radical, alkoxy having 1 to 4 carbon atoms, alkyl having 1 to 4 carbon atoms, trifluoromethyl or trifluoromethoxy, or by an amino group which in turn is substituted by two identical or different substituents from the group consisting of alkyl having 1 to 4 carbon atoms, phenyl or benzyl, $R^3$ and $R^5$, which are identical or different, each represent hydrogen, a straight-chain or branched alkyl radical having up to 4 carbon atoms, a phenyl radical or a benzyl radical, and $R^4$ represents hydrogen, a straight-chain or branched alkyl radical having up to 4 carbon atoms which is optionally interrupted by an oxygen atom, a phenyl radical or a benzyl radical, or a salt thereof with a physiologically tolerated acid.

2. A compound or salt according to claim 1, in which
$R^1$ represents phenyl optionally substituted by one or two indentical or different substituents from the group consisting of fluorine, chlorine, cyano, trifluoromethyl, trifluoromethoxy, alkyl having 1 to 4 C atoms, alkoxy having 1 to 2 C atoms, tetramethylene or phenyl, $R^2$ represents a straight-chain or branched cyclic alkyl or alkenyl radical having up to 12 carbon atoms which is optionally interrupted by an oxygen atom in the chain and/or which is optionally substituted by fluorine, chlorine cyano, hydroxyl, phenyl, phenoxy or an amino group which in turn is substituted by two identical or different substituents from the group consisting of alkyl having 1 to 4 C atoms or benzyl, $R^3$ and $R^5$ are identical or different and each represent alkyl having 1 to 2 C atoms, and $R^4$ represents hydrogen, alkyl having 1 to 4 C atoms or benzyl.

3. A compound or salt according to claim 1, in which
$R^1$ denotes phenyl, chlorophenyl, tolyl, trifluoromethylphenyl, methoxyphenyl, cyanophenyl, trifluoromethoxyphenyl, dichlorophenyl or chlorofluorophenyl, $R^2$ denotes methyl, ethyl, allyl, t-butyl, methoxyethyl, benzyl, benzyloxyethyl or cyanoethyl, $R^3$ and $R^5$ denote methyl, $R^4$ denotes hydrogen and $R^6$ denotes methyl.

4. A compound according to claim 1, wherein such compound is dimethyl 2,6-dimethyl-4-(2-trifluoromethylphenyl)-1,2,3,4-tetrahydropyridine-3,5-dicarboxylate of the formula

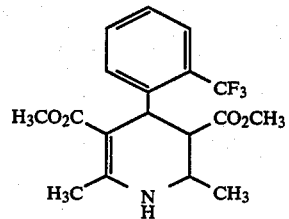

or a salt thereof with a physiologically tolerated acid.

5. A compound according to claim 1, wherein such compound is dimethyl 2,6-dimethyl-4-(2,3-dichlorophenyl)-1,2,3,4-tetrahydropyridine-3,5-dicarboxylate of the formula

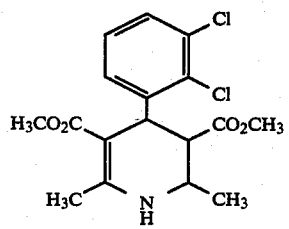

or a salt thereof with a physiologically tolerated acid.

6. An antihypertensive composition which comprises an amount of a compound of claim 1 effective in the treatment of hypertension, and a pharmaceutically acceptable carrier.

7. A composition according to claim 6, in the form of a tablet, capsule or pill containing a unit dose.

8. The method of reducing high blood pressure which comprises administering to a patient suffering therefrom an amount effective therefor of a compound or salt according to claim 1.

9. The method according to claim 8, wherein such compound is
dimethyl 2,6-dimethyl-4-(2-trifluoromethylphenyl)-1,2,3,4-tetrahydropyridine-3,5-dicarboxylate, or
dimethyl 2,6-dimethyl-4-(2,3-dichlorophenyl)-1,2,3,4-tetrahydropyridine-3,5-dicarboxylate, or a salt thereof with a physiologically tolerated acid.

* * * * *